United States Patent
Lee et al.

(10) Patent No.: US 12,049,436 B2
(45) Date of Patent: Jul. 30, 2024

(54) PREPARING METHOD OF COMPOUNDS INCLUDING AMIDE GROUP FROM TERTIARY AMINE

(71) Applicants: RESEARCH & BUSINESS FOUNDATION SUNGKYUNKWAN UNIVERSITY, Suwon-si (KR); INSTITUTE FOR BASIC SCIENCE, Daejeon (KR)

(72) Inventors: Hyoyoung Lee, Suwon-si (KR); Suresh Vasimalla, Suwon-si (KR); Seungeun Lee, Suwon-si (KR)

(73) Assignees: Research & Business Foundation Sungkyunkwan University, Suwon-si (KR); INSTITUTE FOR BASIC SCIENCE, Daejeon (KR)

( * ) Notice: Subject to any disclaimer, the term of this patent is extended or adjusted under 35 U.S.C. 154(b) by 113 days.

(21) Appl. No.: 17/536,383

(22) Filed: Nov. 29, 2021

(65) Prior Publication Data

US 2022/0177416 A1    Jun. 9, 2022

(30) Foreign Application Priority Data

Nov. 27, 2020  (KR) .......................... 10-2020-0162049

(51) Int. Cl.
| | | |
|---|---|---|
| *C07C 231/10* | (2006.01) | |
| *B01J 21/06* | (2006.01) | |
| *B01J 35/39* | (2024.01) | |
| *B01J 37/16* | (2006.01) | |
| *C01G 23/08* | (2006.01) | |
| *C07C 233/65* | (2006.01) | |
| *C07D 295/192* | (2006.01) | |
| *C07D 401/04* | (2006.01) | |

(52) U.S. Cl.
CPC .......... *C07C 231/10* (2013.01); *B01J 21/063* (2013.01); *B01J 35/39* (2024.01); *B01J 37/16* (2013.01); *C01G 23/08* (2013.01); *C07C 233/65* (2013.01); *C07D 295/192* (2013.01); *C07D 401/04* (2013.01)

(58) Field of Classification Search
CPC .................................................. C07C 231/10
See application file for complete search history.

(56) References Cited

FOREIGN PATENT DOCUMENTS

KR    10-1907124 B1    10/2018

OTHER PUBLICATIONS

Pinnick, H. W. Comprehensive Organic Synthesis, vol. 7, 1991, 2.5 Oxidation Adjacent to Nitrogen, pp. 217-234 (Year: 1991).*
Dai et al. Comprehensive Organic Synthesis (Second Edition), vol. 7, 2014, pp. 242-261 (Year: 2014).*
Dorwald, F. Zaragoza. Side Reactions in Organic Synthesis: A Guide to Successful Synthesis Design, Weinheim: Wiley-VCH Verlag GmbH & Co. KGaA, 2005, Preface (Year: 2005).*
Baxendale, Ian R et al., "Synthesis of Nornicotine, Nicotine and Other Functionalised Derivatives Using Solid-Supported Reagents and Scavengers," Journal of the Chemical Society, Perkin Transactions 1, 2002, (pp. 143-154).
Byun, Jang-Woong et al., "Preparation of Polymer-Bound Pyrazolone Active Esters For Combinatorial Chemistry," Tetrahedron Letters, vol. 44, Issue 44, 2003, (5 Pages in English).
Li, Yuanming et al., "Iron-Catalyzed Oxidative Amidation of Tertiary Amines with Aldehydes," Chemistry, European Journal, 2012, (6 Pages in English).
Mai, Wen-Peng et al., "Nbu4ni-Catalyzed Unexpected Amide Bond Formation Between Aldehydes and Aromatic Tertiary Amines," RSC Advances, Jan. 25, 2013, (pp. 3869-3872).
Mohammad, Akbar et al., "Facile Access to Amides from Oxygenated or Unsaturated Organic Compounds by Metal Oxide Nanocatalysts Derived from Single-Source Molecular Precursors," American Chemical Society, 2017, (p. 10596-10608).

* cited by examiner

*Primary Examiner* — Matthew P Coughlin
(74) *Attorney, Agent, or Firm* — NSIP Law

(57) ABSTRACT

Provided is a preparing method of an amide directly from a tertiary amine by using a reduced titanium dioxide (Blue $TiO_2$), which is formed by mixing a titanium dioxide having an anatase phase and a rutile phase with a reducing agent and selectively reducing any one of the anatase phase and the rutile phase, as a photocatalyst.

9 Claims, 4 Drawing Sheets

[Fig.1]
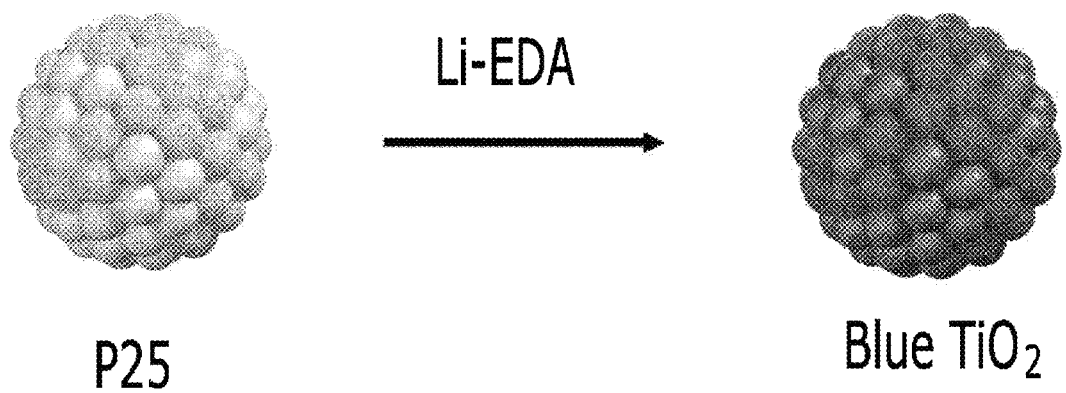

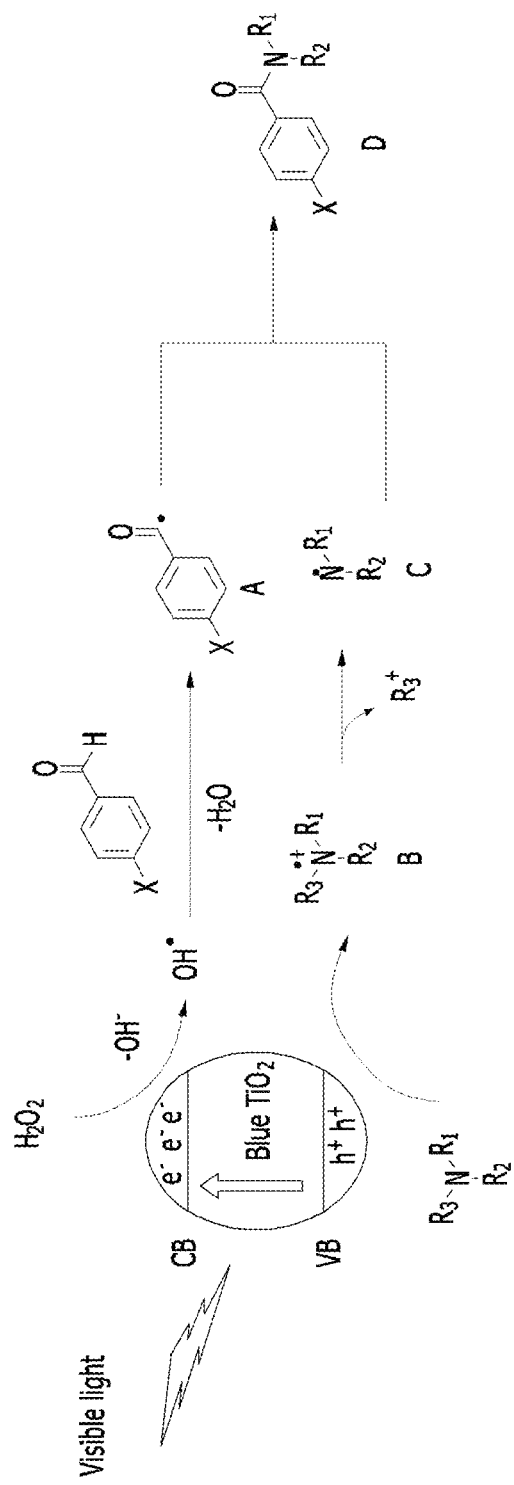
[Fig. 2]

[Fig.3]
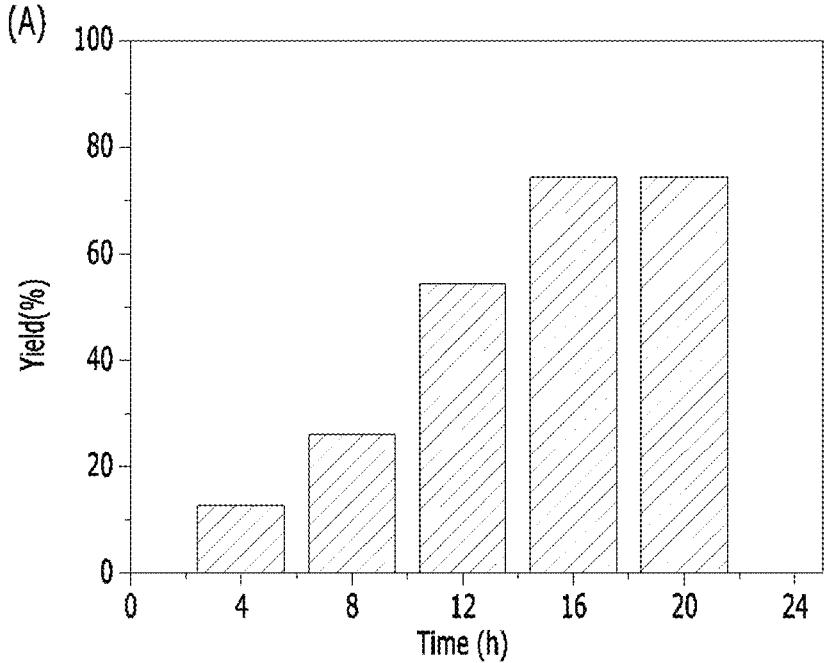
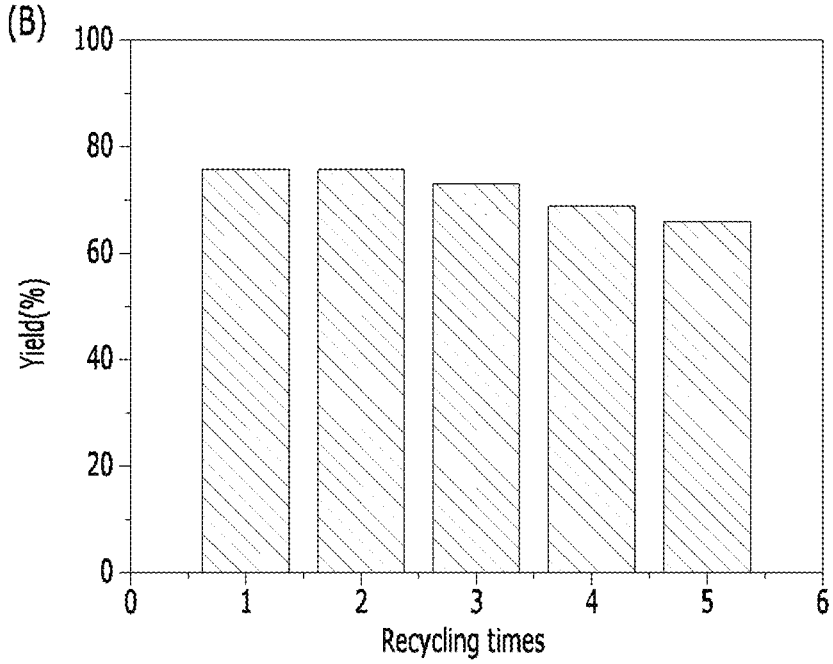

[Fig.4]
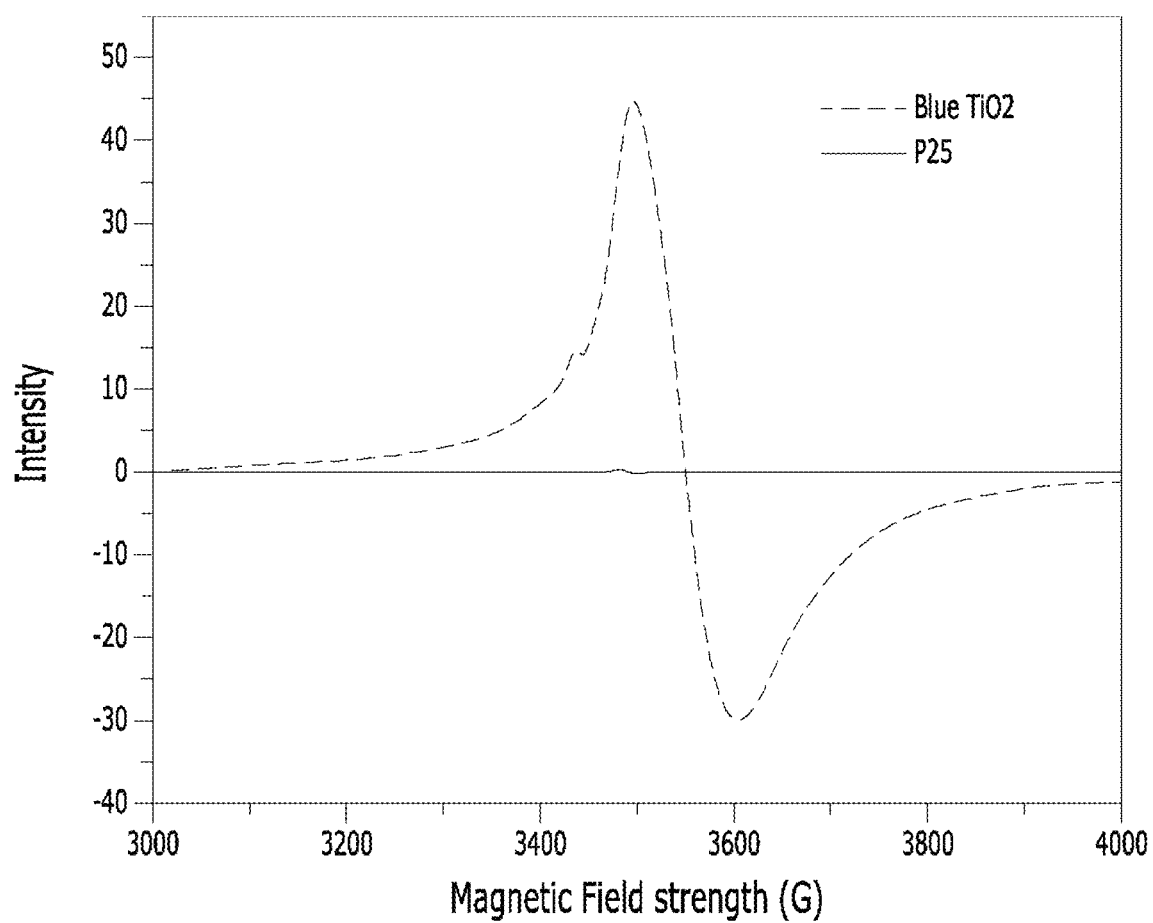

PREPARING METHOD OF COMPOUNDS INCLUDING AMIDE GROUP FROM TERTIARY AMINE

CROSS REFERENCE TO RELATED APPLICATIONS

This application claims the benefit under 35 USC 119(a) of Korean Patent Application No. 10-2020-0162049 filed on Nov. 27, 2020, in the Korean Intellectual Property Office, the entire disclosures of which are incorporated herein by reference for all purposes.

BACKGROUND

Field

The present disclosure relates to a preparing method of compounds including an amide group from a tertiary amine.

Description of the Related Art

25% or more of the drugs currently known on Earth have amide bonds. General methods for synthesizing a compound having an amide bond include reactions among a primary amine, a secondary amine, a carboxylic acid and their derivatives. These methods have some problems such as low atomization efficiency, use of hazardous reagents and formation of by-products that cause environmental problems.

To synthesize a compound including an amide group, various methods, such as Staudinger reaction, Schmidt reaction, Beckmann rearrangement, aminocarbonylation of aryl halides, and coupling between α-halo nitro alkane and amine using iodonium as an activation agent, have been developed.

Aryl halides, nitriles, oxides and alkynes are converted into amides using a transition metal catalyst so that it is possible to avoid the use of unstable functional groups. When a carboxylic acid is used, a by-product is produced. Therefore, a method for synthesizing amide directly from aldehyde using iodine, NBS, manganese oxide, 3,3',5,5'-tetra-tert-butyldiphenoquinone (DPQ) and tert-butyl hydroperoxide (TBHP) as an oxidizing agent has been developed. However, this method is performed under high temperature and severe reaction conditions, and most of the methods are limited to primary and secondary amines.

Tertiary amines are widely found in natural products and can be obtained more stably and easily than primary and secondary amines. Meanwhile, tertiary amines are less electrophilic, and, thus, the oxidative amidation of tertiary amines generally requires severe conditions and uses expensive metal catalysts such as palladium, ruthenium and iridium, which cannot meet the industrial demands for cost-effective methods.

Korean Patent No. 10-1907124 relates to a reduced titanium dioxide (Blue $TiO_2$) photocatalyst which is formed by selectively reducing any one of an anatase phase and a rutile phase included in a titanium dioxide. Unlike the present disclosure, Korean Patent No. 10-1907124 describes only a process for preparing the photocatalyst but does not describe a method for preparing a compound including an amide group from a tertiary amine by using the photocatalyst.

SUMMARY

An object to be achieved by the present disclosure is to provide a preparing method of a compound including an amide group directly from a tertiary amine at room temperature by using a reduced titanium dioxide (Blue $TiO_2$), which is formed by reducing only any one of an anatase phase and a rutile phase, as a photocatalyst unlike a conventional method of synthesizing an amide group from primary and secondary amines under high temperature and severe reaction conditions.

Further, another object to be achieved by the present disclosure is to provide a preparing method of a compound including an amide group using the reduced titanium dioxide (Blue $TiO_2$) as a photocatalyst unlike a conventional method of preparing a compound including an amide group from a tertiary amine by using an expensive metal catalyst.

Yet another object to be achieved by the present disclosure is to provide a preparing method of a compound including an amide group by reacting a tertiary amine with aldehyde using the reduced titanium dioxide (Blue $TiO_2$) as a photocatalyst.

Still another object to be achieved by the present disclosure is to provide a preparing method of a compound including an amide bond which is prepared by the reaction between a tertiary amine with aldehyde using the reduced titanium dioxide (Blue $TiO_2$) as a photocatalyst.

The objects of the present disclosure are not limited to the above-described objects, and there may be other objects of the present disclosure.

According to a first aspect of the present disclosure, there is provided a preparing method of a compound including an amide group, including a process of forming a reduced titanium dioxide which is formed by mixing a titanium dioxide ($TiO_2$) having an anatase phase and a rutile phase with a reducing agent and selectively reducing any one of the anatase phase and the rutile phase and a process of preparing a compound including an amide group by reacting a tertiary amine in the presence of the reduced titanium dioxide.

According to an embodiment of the present disclosure, the process of preparing a compound including an amide group by reacting a tertiary amine in the presence of the reduced titanium dioxide may include a process of reacting the tertiary amine with a compound including an aldehyde group, but may not be limited thereto.

According to an embodiment of the present disclosure, the process of preparing a compound including an amide group by reacting a tertiary amine in the presence of the reduced titanium dioxide may include a process of irradiating light and performing a reaction using the reduced titanium dioxide as a photocatalyst, but may not be limited thereto.

According to an embodiment of the present disclosure, the process of preparing a compound including an amide group by reacting a tertiary amine in the presence of the reduced titanium dioxide may include a process of adding an electron acceptor, but may not be limited thereto.

According to an embodiment of the present disclosure, the electron acceptor may include hydrogen peroxide ($H_2O_2$), tert-Butyl hydroperoxide (TBHP), dioxane, ammonium persulfate (($NH_4$)$_2S_2O_8$) or potassium bromide ($KBrO_3$), but may not be limited thereto.

According to an embodiment of the present disclosure, the tertiary amine may include a compound represented by Chemical Formula 1, Chemical Formula 2 or Chemical Formula 3, but may not be limited thereto:

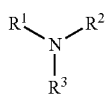

[Chemical Formula 1]

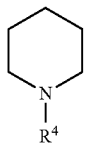

[Chemical Formula 2]

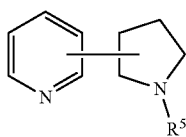

[Chemical Formula 3]

(in Chemical Formulas 1 to 3, $R^1$, $R^2$, $R^3$, $R^4$ and $R^5$ each represent independently linear or branched substituted $C_1$-$C_{20}$ alkyl, or substituted $C_6$-$C_{24}$ aryl; and the substitution may include substitution with oxygen, nitrogen, sulfur, linear or branched $C_1$-$C_6$ alkyl, $C_6$-$C_{20}$ aryl, halogen, alkoxy, trimethylsilyl, or ether, but may not be limited thereto).

According to an embodiment of the present disclosure, the compound including an aldehyde group may include a compound represented by Chemical Formula 4 or Chemical Formula 5, but may not be limited thereto:

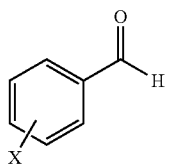

[Chemical Formula 4]

(in Chemical Formula 4, X may include $NO_2$, CN, $NH_2$, $SO_3H$, linear or branched substituted $C_1$-$C_{20}$ alkyl, or substituted $C_6$-$C_{24}$ aryl, but may not be limited thereto); and

  $R^6CHO$                     [Chemical Formula 5]

(in Chemical Formula 5, $R^6$ may be linear or branched substituted $C_1$-$C_{20}$ alkyl, or substituted $C_6$-$C_{24}$ aryl, but may not be limited thereto).

According to an embodiment of the present disclosure, the process of preparing a compound including an amide group by reacting a tertiary amine in the presence of the reduced titanium dioxide may be performed at room temperature, but may not be limited thereto.

According to an embodiment of the present disclosure, the reducing agent may include alkali metals and amines, but may not be limited thereto.

According to an embodiment of the present disclosure, the alkali metals may include a metal selected from the group consisting of Li, Na, K and combinations thereof, but may not be limited thereto.

According to an embodiment of the present disclosure, the amines may include a liquid ammonium-based material selected from the group consisting of ethylenediamine, propylenediamine, methylenediamine, ethylamine, 1 2-dimethoxyethane, hexamethyleneimine, diisopropylamide, diethanolamine, polyethyleneamine and combinations thereof, a member selected from the group consisting of ethylenediaminetetraacetic acid, diethylenetriamine pentaacetic acid, diaminohydroxypropane tetraacetic acid and combinations thereof, or a liquid amine for forming solvated electrons, selected from the group consisting of tetrahydrofuran, dimethyl sulfoxide, hexamethylphosphoramide, diethylamine, triethylamine, diethylenetriamine, toluenediamine, m-phenylenediamine, diphenylmethane diamine, hexamethylenediamine, triethylenetetramine, tetraethylenepentamine, hexamethylenetetramine, ethanolamine, diethanolamine, triethanolamine and combinations thereof, but may not be limited thereto.

According to an embodiment of the present disclosure, the reduction may be performed in a sealed and anhydrous state, but may not be limited thereto.

According to an embodiment of the present disclosure, the reduction may be performed at room temperature, but may not be limited thereto.

According to a second aspect of the present disclosure, there is provided a titanium dioxide photocatalyst including a reduced titanium dioxide ($TiO_2$) photocatalyst which is formed by selectively reducing any one of an anatase phase and a rutile phase, and the titanium dioxide photocatalyst may be a reaction catalyst of a tertiary amine and a compound including an aldehyde group.

According to a third aspect of the present disclosure, there is provided a compound including an amide group and prepared by reacting a tertiary amine with a compound including an aldehyde group in the presence of the titanium dioxide photocatalyst according to the second aspect.

According to an embodiment of the present disclosure, the compound including an amide group may include a compound including an amide group represented by Chemical Formula 6, Chemical Formula 7 or Chemical Formula 8, but may not be limited thereto:

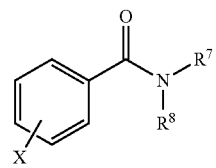

[Chemical Formula 6]

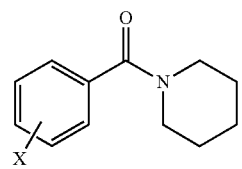

[Chemical Formula 7]

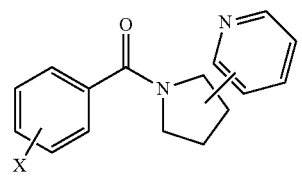

[Chemical Formula 8]

(in Chemical Formulas 6 to 8, $R^7$ and $R^8$ each represent independently linear or branched substituted $C_1$-$C_{20}$ alkyl, or substituted $C_6$-$C_{24}$ aryl;

the substitution may include substitution with oxygen, nitrogen, sulfur, linear or branched $C_1$-$C_6$ alkyl, $C_6$-$C_{20}$ aryl, halogen, alkoxy, trimethylsilyl, or ether, but may not be limited thereto; and in Chemical Formulas 6 to 8, X may be $NO_2$, CN, $NH_2$, $SO_3H$, linear or branched substituted $C_1$-$C_{20}$ alkyl, or substituted $C_6$-$C_{24}$ aryl, but may not be limited thereto).

The above-described aspects are provided by way of illustration only and should not be construed as liming the present disclosure. Besides the above-described exemplary embodiments, there may be additional exemplary embodiments described in the accompanying drawings and the detailed description.

In a conventional preparing method of a compound including an amide group, a compound including an amide group is prepared through a coupling reaction of a primary amine or secondary amine and aldehyde in the presence of a complex of two or more metal catalysts or an iridium or ruthenium photocatalyst including an organic material.

A titanium dioxide catalyst according to the present disclosure is a single metal catalyst without an additional organic material or metal catalyst unlike conventionally know iridium and ruthenium photocatalysts, and facilitates effective preparation of a compound including aldehyde and an amide group by using primary, secondary and tertiary amines.

The preparing method of a compound including an amide group through the reaction between aldehyde and a tertiary amine, which is more stable and has a lower reactivity than primary amine and secondary amines, can be performed at room temperature unlike the conventional method that is performed under severe reaction conditions. Accordingly, a tertiary amine, which has a lower reactivity and is more stable than primary and secondary amines, is used, and a compound including an amide group is expected to be synthesized even in a reaction with a compound including a ketone group instead of aldehyde due to a high efficiency of the titanium dioxide photocatalyst.

Further, a titanium dioxide (Blue $TiO_2$) formed by reducing only any one of an anatase phase and a rutile phase according to the present disclosure has a small band gap. Therefore, it is easy to generate an amide bond through a radical mechanism for a coupling reaction between aldehyde and a tertiary amine.

Furthermore, the reduced titanium dioxide (Blue $TiO_2$) according to the present disclosure can be used as a photocatalyst under visible light unlike P-25 $TiO_2$, which is a conventional photocatalyst, and can reduce a material repeatedly for a long time.

The effects to be achieved by the present disclosure are not limited to the above-described effects, and there may be other effects of the present disclosure.

BRIEF DESCRIPTION OF THE DRAWINGS

The above and other aspects, features and other advantages of the present disclosure will be more clearly understood from the following detailed description taken in conjunction with the accompanying drawings, in which:

FIG. 1 shows a process of forming a titanium dioxide (Blue $TiO_2$) by reducing only any one of an anatase phase and a rutile phase according to an exemplary embodiment of the present disclosure;

FIG. 2 shows a mechanism for preparing a compound including an amide bond according to an example of the present disclosure;

(A) of FIG. 3 is a graph showing the changes in yield of a product over reaction time according to an example of the present disclosure, and (B) of FIG. 3 is a graph showing the changes in yield of a product depending on the number of uses of a catalyst; and FIG. 4 is a graph showing EPR spectra of P25 $TiO_2$ and a reduced titanium dioxide (Blue $TiO_2$) after irradiation of light from a CFL lamp according to a test example of the present disclosure.

DETAILED DESCRIPTION OF THE EMBODIMENT

Hereafter, exemplary embodiments will be described in detail with reference to the accompanying drawings so that the present disclosure may be readily implemented by a person with ordinary skill in the art.

However, it is to be noted that the present disclosure is not limited to the exemplary embodiments but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Through the whole document, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereafter, a preparing method of a compound including an amide group from a tertiary amine of the present disclosure will be described in detail with reference to embodiments, examples and the accompanying drawings. However, the present disclosure is not limited to the following embodiments, examples and drawings.

According to a first aspect of the present disclosure, there is provided a preparing method of a compound including an amide group, including a process of forming a reduced titanium dioxide which is formed by mixing a titanium dioxide (TiO$_2$) having an anatase phase and a rutile phase with a reducing agent and selectively reducing any one of the anatase phase and the rutile phase and a process of preparing a compound including an amide group by reacting a tertiary amine in the presence of the reduced titanium dioxide.

25% or more of the drugs currently known on Earth have amide bonds. Conventional general methods for synthesizing amide include reactions among a primary amine, a secondary amine, a carboxylic acid and their derivatives. These methods have some problems, such as low atomization efficiency, use of hazardous reagents and formation of by-products that cause environmental problems, and require severe reaction conditions.

Also, most of the methods are limited to primary and secondary amines. Tertiary amines can be obtained more stably and easily than primary and secondary amines. Meanwhile, tertiary amines are less electrophilic and thus require severe conditions and metal catalysts for reaction.

According to an embodiment of the present disclosure, the compound including an amide group is directly prepared by reacting a tertiary amine and aldehyde using the reduced titanium dioxide as a photocatalyst in the presence of visible light. Also, this preparing method is performed at room temperature and thus is easier to perform than a conventional method of preparing an amide group from a tertiary amine.

FIG. 1 shows a process of forming a reduced titanium dioxide (Blue TiO$_2$) by selectively reducing any one of an anatase phase and a rutile phase included in a titanium dioxide (P25) according to an exemplary embodiment of the present disclosure.

Specifically, the reduced titanium dioxide (Blue TiO$_2$) shown in FIG. 1 is blue in color, but may not be limited thereto.

According to an embodiment of the present disclosure, the process of preparing a compound including an amide group by reacting a tertiary amine in the presence of the reduced titanium dioxide may include a process of reacting the tertiary amine with a compound including an aldehyde group, but may not be limited thereto.

According to an embodiment of the present disclosure, the process of preparing a compound including an amide group by reacting a tertiary amine in the presence of the reduced titanium dioxide may include a process of irradiating light and performing a reaction using the reduced titanium dioxide as a photocatalyst, but may not be limited thereto. For example, visible light may be irradiated from a CFL lamp, but may not be limited thereto.

According to an embodiment of the present disclosure, the process of preparing a compound including an amide group by reacting a tertiary amine in the presence of the reduced titanium dioxide may include a process of adding an electron acceptor, but may not be limited thereto.

According to an embodiment of the present disclosure, the electron acceptor may include hydrogen peroxide (H$_2$O$_2$), tert-Butyl hydroperoxide (TBHP), dioxane, ammonium persulfate ((NH$_4$)$_2$S$_2$O$_8$) or potassium bromide (KBrO$_3$), but may not be limited thereto.

According to an embodiment of the present disclosure, the tertiary amine may include a compound represented by Chemical Formula 1, Chemical Formula 2 or Chemical Formula 3, but may not be limited thereto:

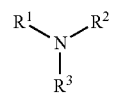

[Chemical Formula 1]

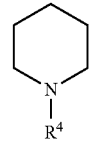

[Chemical Formula 2]

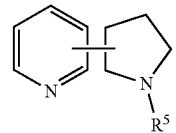

[Chemical Formula 3]

(in Chemical Formulas 1 to 3, R$^1$, R$^2$, R$^3$, R$^4$ and R$^5$ each represent independently linear or branched substituted C$_1$-C$_{20}$ alkyl, or substituted C$_6$-C$_{24}$ aryl; and the substitution may include substitution with oxygen, nitrogen, sulfur, linear or branched C$_1$-C$_6$ alkyl, C$_6$-C$_{20}$ aryl, halogen, alkoxy, trimethylsilyl, or ether, but may not be limited thereto).

According to an embodiment of the present disclosure, the compound including an aldehyde group may include a compound represented by Chemical Formula 4 or Chemical Formula 5, but may not be limited thereto:

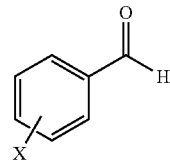

[Chemical Formula 4]

(in Chemical Formula 4, X may include NO$_2$, CN, NH$_2$, SO$_3$H, linear or branched substituted C$_1$-C$_{20}$ alkyl, or substituted C$_6$-C$_{24}$ aryl, but may not be limited thereto); and R$^6$CHO  [Chemical Formula 5]

(in Chemical Formula 5, R$^6$ may be linear or branched substituted C$_1$-C$_{20}$ alkyl, or substituted C$_6$-C$_{24}$ aryl, but may not be limited thereto).

Reaction Formula 1 shows an exemplary process of preparing a compound including an amide group by reacting the tertiary amine with a compound including aldehyde in the presence of the reduced titanium dioxide according to an example of the present disclosure:

[Reaction Formula 1]

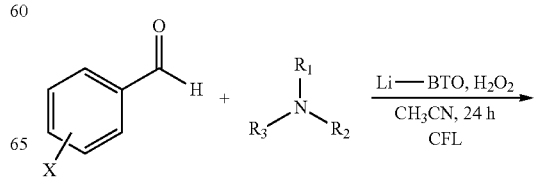

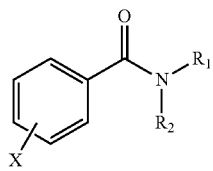

(in Reaction Formula 1, $R^1$, $R^2$, and $R^3$ each represent independently linear or branched substituted $C_1$-$C_{20}$ alkyl, or substituted $C_6$-$C_{24}$ aryl;

the substitution may include substitution with oxygen, nitrogen, sulfur, linear or branched $C_1$-$C_6$ alkyl, $C_6$-$C_{20}$ aryl, halogen, alkoxy, trimethylsilyl, or ether; and X may include $NO_2$, CN, $NH_2$, $SO_3H$, linear or branched substituted $C_1$-$C_{20}$ alkyl, or substituted $C_6$-$C_{24}$ aryl).

FIG. 2 shows a specific process in which the reduced titanium dioxide prepared according to Reaction Formula 1 serves as a photocatalyst and an electron acceptor is added to prepare a compound including an amide bond by reacting a tertiary amine and aldehyde through a radical mechanism.

Specifically, after light irradiation, the reduced titanium dioxide (Blue $TiO_2$) forms an electron and a hole in conduction band and valence band, and the electron generates an OH radical with $H_2O_2$. The generated OH radical extracts a hydrogen atom from aldehyde and generates a carbonyl radical A.

Further, the hole in the valence band forms an amine radical cation B with the tertiary amine, and the radical cation B generates an amine radical C.

Finally, the amine radical C and the carbonyl radical A form an amide bond so that a compound D including the amide bond is generated.

According to an embodiment of the present disclosure, the process of preparing a compound including an amide group by reacting a tertiary amine in the presence of the reduced titanium dioxide may be performed at room temperature, but may not be limited thereto.

According to an embodiment of the present disclosure, the reducing agent may include alkali metals and amines, but may not be limited thereto.

According to an embodiment of the present disclosure, the alkali metals may include a metal selected from the group consisting of Li, Na, K and combinations thereof, but may not be limited thereto.

According to an embodiment of the present disclosure, the amines may include a liquid ammonium-based material selected from the group consisting of ethylenediamine, propylenediamine, methylenediamine, ethylamine, 1,2-dimethoxyethane, hexamethyleneimine, diisopropylamide, diethanolamine, polyethyleneamine and combinations thereof, a member selected from the group consisting of ethylenediaminetetraacetic acid, diethylenetriamine pentaacetic acid, diaminohydroxypropane tetraacetic acid and combinations thereof, or a liquid amine for forming solvated electrons, selected from the group consisting of tetrahydrofuran, dimethyl sulfoxide, hexamethylphosphoramide, diethylamine, triethylamine, diethylenetriamine, toluenediamine, m-phenylenediamine, diphenylmethane diamine, hexamethylenediamine, triethylenetetramine, tetraethylenepentamine, hexamethylenetetramine, ethanolamine, diethanolamine, triethanolamine and combinations thereof, but may not be limited thereto.

According to an embodiment of the present disclosure, the reduction may be performed in a sealed and anhydrous state, but may not be limited thereto.

According to an embodiment of the present disclosure, the reduction may be performed at room temperature, but may not be limited thereto.

According to a second aspect of the present disclosure, there is provided a titanium dioxide photocatalyst including a reduced titanium dioxide ($TiO_2$) photocatalyst which is formed by selectively reducing any one of an anatase phase and a rutile phase, and the titanium dioxide photocatalyst may be a reaction catalyst of a tertiary amine and a compound including an aldehyde group.

Detailed descriptions of the titanium dioxide photocatalyst according to the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

According to a third aspect of the present disclosure, there is provided a compound including an amide group and prepared by reacting a tertiary amine with a compound including an aldehyde group in the presence of the titanium dioxide photocatalyst according to the second aspect.

Detailed descriptions of the compound including an amide group according to the third aspect of the present disclosure, which overlap with those of the first aspect of the present disclosure, are omitted hereinafter, but the descriptions of the first aspect of the present disclosure may be identically applied to the third aspect of the present disclosure, even though they are omitted hereinafter.

According to an embodiment of the present disclosure, the compound including an amide group may include a compound including an amide group represented by Chemical Formula 6, Chemical Formula 7 or Chemical Formula 8, but may not be limited thereto:

[Chemical Formula 6]

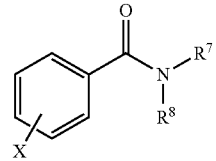

[Chemical Formula 7]

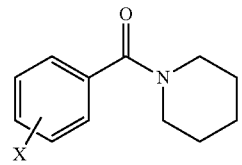

[Chemical Formula 8]

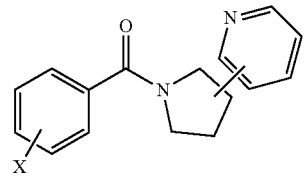

(in Chemical Formulas 6 to 8, $R^7$ and $R^8$ each represent independently linear or branched substituted $C_1$-$C_{20}$ alkyl, or substituted $C_6$-$C_{24}$ aryl;

the substitution may include substitution with oxygen, nitrogen, sulfur, linear or branched $C_1$-$C_6$ alkyl, $C_6$-$C_{20}$ aryl, halogen, alkoxy, trimethylsilyl, or ether, but may not be limited thereto; and in Chemical Formulas 6 to 8, X may be $NO_2$, CN, $NH_2$, $SO_3H$, linear or branched substituted $C_1$-$C_{20}$ alkyl, or substituted $C_6$-$C_{24}$ aryl, but may not be limited thereto).

Hereinafter, the present disclosure will be described in more detail with reference to examples. The following examples are provided only for explanation, but do not intend to limit the scope of the present disclosure.

[Example 1]: Preparation of Photocatalyst

A titanium dioxide (Blue $TiO_2$) photocatalyst formed by reducing only any one of an anatase phase and a rutile phase was prepared according to a previously reported procedure.

Specifically, 14 mg of metallic Li foil was dissolved in 20 ml of ethylenediamine to form a 1 mmol/ml solvated electron solution. 200 mg of dried $TiO_2$ nanoparticles (anatase, size: 25 nm or less, rutile, size: 140 nm or less, P-25, size: 20 nm to 40 nm) was added into the solution and stirred for 7 days. The reaction was performed in a sealed and anhydrous state.

Then, a 1 mol/L HCl was slowly added into the mixture to quench the excess electrons and form Li salts. Finally, the produced composite was rinsed by deionized water several times and dried at room temperature in a vacuum oven to prepare the reduced titanium dioxide (Blue $TiO_2$).

Comparative Example

Various photocatalysts were used as comparative examples for comparison in performance with the photocatalyst according to an example of the present disclosure.

Specifically, P25 $TiO_2$, Black $TiO_2$, Anatase $TiO_2$ and Rutile $TiO_2$ were used for comparison in performance with the photocatalyst according to an example of the present disclosure.

[Example 2]: Preparation of Compound Including Amide Group Using Photocatalyst

Table 1 shows the results of reactions between 4-nitro benzaldehyde (1a) and N, N-diisopropylethylamine (1b) to form 4-nitro N, N-diisopropyl-benzamide while changing the photocatalyst (Blue $TiO_2$) according to the example of the present disclosure, the photocatalysts (P25 $TiO_2$, Black $TiO_2$, Anatase and Rutile) according to the comparative example, the equivalent ratio of aldehyde to amine, a solvent, and an electron acceptor.

TABLE 1

| Entry | Cayalyst | 1a(eq) | 1b(eq) | Solvent | Additive | Yield(%) |
|---|---|---|---|---|---|---|
| 1 | Blue $TiO_2$ | 1 | 6 | $CH_3CN$ | $H_2O_2$ | 75 |
| 2 | Blue $TiO_2$ | 1 | 4 | $CH_3CN$ | $H_2O_2$ | 45 |
| 3 | Blue $TiO_2$ | 1 | 2 | $CH_3CN$ | $H_2O_2$ | 20 |
| 4 | Blue $TiO_2$ | 1 | 10 | $CH_3CN$ | $H_2O_2$ | 75 |
| 5 | P25 $TiO_2$ | 1 | 6 | $CH_3CN$ | $H_2O_2$ | 10 |
| 6 | Black $TiO_2$ | 1 | 6 | $CH_3CN$ | $H_2O_2$ | 6 |
| 7 | Anatase | 1 | 6 | $CH_3CN$ | $H_2O_2$ | 5 |
| 8 | Rutile | 1 | 6 | $CH_3CN$ | $H_2O_2$ | 3 |
| 9 | Blue $TiO_2$ | 1 | 6 | $CH_3CN$ | TBHP | 20 |
| 10 | Blue $TiO_2$ | 1 | 6 | $CH_3CN$ | Dioxane | 0 |
| 11 | Blue $TiO_2$ | 1 | 6 | Acetone | $H_2O_2$ | 0 |
| 12 | Blue $TiO_2$ | 1 | 6 | $CHCl_3$ | $H_2O_2$ | 0 |
| 13 | Blue $TiO_2$ | 1 | 6 | DCM | $H_2O_2$ | 0 |

Referring to Table 1, at an initial equivalent ratio of 1:2 of aldehyde to tertiary amine, the yield was 20% (Entry 3), and as the ratio of aldehyde to tertiary amine increases to 1:4 and 1:6 (Entry 2 and Entry 1), the yield increased to 45% and 75%, respectively. Although the equivalent of amine increased from 6 to 10 by comparison between Entry 1 and Entry 4, the yield did not increase.

Also, to check the yield depending on the type of catalyst at the ratio of 1:6 of aldehyde to amine, each of Blue $TiO_2$, P25 $TiO_2$, Black $TiO_2$, and Anatase and Rutile (Entry 5, Entry 6, Entry 7, and Entry 8) was used as a catalyst for reaction, and the resultant yields were 75%, 10%, 6%, 5%, and 3%, respectively. The highest yield was obtained when Blue $TiO_2$ (Entry 1) was used.

Further, an electron acceptor was used to generate radicals from $TiO_2$. To check the yield depending on the type of electron acceptor, each of hydrogen peroxide ($H_2O_2$), tert-Butyl hydroperoxide (TBHP), and dioxane (Entry 1, Entry 9, and Entry 10) was used as an electron acceptor, and the resultant yields were 75%, 20%, and 0%, respectively. The highest yield was obtained when H$_2$O$_2$(Entry 1) was used as a solvent under the same conditions.

Furthermore, to check the yield depending on the type of solvent, each of CH$_3$CN, acetone, CHCl$_3$ and CH$_2$Cl$_2$ (DCM) (Entry 1, Entry 11, Entry 12, and Entry 13) was used, and the resultant yields of Entries were 0% except Entry 1. The yield was 75% when CH$_3$CN (Entry 1) was used.

Referring to Table 1, it can be seen that the highest yield was obtained when Blue TiO$_2$ was used as a catalyst, CH$_3$CN was used as a solvent and H$_2$O$_2$ was used as an electron acceptor at a ratio of 1:6 of aldehyde to amine.

Table 2 shows the results of reactions between 4-nitro benzaldehyde (1a) and N, N-diisopropylethylamine (1b) without light or H$_2$O$_2$ as an electron acceptor or with TEMPO as a radical scavenger.

Referring to Table 2, the yield was trace under no light conditions (Entry 1). This means that light is needed to promote the reaction.

Also, no product was produced in the absence of H$_2$O$_2$ (Entry 2). This means that an electron acceptor is needed to make the reduced titanium dioxide serve as a photocatalyst.

Further, when TEMPO was used as a radical scavenger (Entry 3), no product was produced. This teaches that the reaction is of radical type.

It was found from Example 2 that the standard reaction conditions are the ratio of 1:6 of aldehyde to amine, 10 mmol catalyst and 4 equivalents of H$_2$O$_2$ in the presence of CFL light. Also, it was found that all of light, H$_2$O$_2$ and Blue TiO$_2$ are essential for the reaction.

Example 3

Table 3-1 and Table 3-2 show the results of reactions with different types of aldehyde and amine to check the applicability of reactions for preparing a compound including an amide group by reacting amine and aldehyde in the presence of the reduced titanium dioxide.

TABLE 2

| Entry | Aldehyde | Amine | Condition | Yield |
|---|---|---|---|---|
| 1 | 1a | 1b | No Light | Trace amount |
| 2 | 1a | 1b | No H$_2$O$_2$ | 0 |
| 3 | 1a | 1b | TEMPO | 0 |

TABLE 3-1

| Entry | Aldehyde | Amine | Product | Yield (%) |
|---|---|---|---|---|
| 1 | 4-nitrobenzaldehyde | diisopropylethylamine | 1c | 75 |
| 2 | 4-nitrobenzaldehyde | triethylamine | 2c | 65 |
| 3 | 4-nitrobenzaldehyde | N-tert-butyl-N-methylethylamine | 3c | 57 |
| 4 | 4-nitrobenzaldehyde | tributylamine | 4c | 70 |
| 5 | 3-nitrobenzaldehyde | diisopropylethylamine | 5c | 70 |

TABLE 3-1-continued

| Entry | Aldehyde | Amine | Product | | Yield (%) |
|---|---|---|---|---|---|
| 6 | 4-nitrobenzaldehyde | dicyclohexylamine | N,N-dicyclohexyl-4-nitrobenzamide | 6c | 62 |
| 7 | 3-nitrobenzaldehyde | aniline | N,N-dibutyl-3-nitrobenzamide | 8c | 66 |
| 8 | 3-nitrobenzaldehyde | tributylamine | N,N-dibutyl-3-nitrobenzamide | 8c | 73 |

TABLE 3-2

| Entry | Aldehyde | Amine | Product | | Yield (%) |
|---|---|---|---|---|---|
| 9 | 2-nitrobenzaldehyde | N,N-diisopropylethylamine | N,N-diisopropyl-2-nitrobenzamide | 9c | 69 |
| 10 | 4-nitrobenzaldehyde | diisopropylamine | N,N-diisopropyl-4-nitrobenzamide | 10c | 70 |
| 11 | 4-nitrobenzaldehyde | 1-methylpiperidine | (4-nitrophenyl)(piperidin-1-yl)methanone | 11c | 59 |
| 12 | 2-nitrobenzaldehyde | tributylamine | N,N-dibutyl-2-nitrobenzamide | 12c | 15 |

TABLE 3-2-continued

| Entry | Aldehyde | Amine | Product | Yield (%) |
|---|---|---|---|---|
| 13 | 4-cyanobenzaldehyde | butylamine | 13c: 4-cyano-N-butylbenzamide | 73 |
| 14 | 4-cyanobenzaldehyde | triethylamine | 14c: 4-cyano-N,N-diethylbenzamide | 67 |
| 15 | 4-cyanobenzaldehyde | N-methylpiperidine | 15c: (4-cyanophenyl)(piperidin-1-yl)methanone | 61 |
| 16 | 4-cyanobenzaldehyde | tributylamine | 16c: 4-cyano-N,N-dibutylbenzamide | 69 |

The applicability of reactions under the standard reaction conditions (the ratio of 1:6 of aldehyde to amine, 10 mmol catalyst and 4 equivalents of $H_2O_2$) was checked from Example 2.

An influence depending on the location of a functional group present on an aromatic ring was checked. To this end, the reaction between 3-nitro benzaldehyde and 2-nitro benzaldehyde was conducted. It was confirmed that the two groups acted well so that the reaction was not influenced by the location of a functional group present on an aromatic ring.

Then, an influence depending on the type of a substituent group present on an aromatic ring was checked. The applicability of reactions was checked using aldehyde that has $NO_2$, CN, F, Cl, Br, OH, Me and OMe substituent groups at respective para sites on an aromatic ring. An amide bond was not formed when the compounds having F, Cl, Br, OH, Me and OMe substituent groups, respectively, were used. This may be because radicals generated during the reaction were less stable and did not react due to +I effect of these functional groups. Meanwhile, aldehydes having $NO_2$ and CN substituent groups exhibited a high yield.

Referring to Table 3-1 and Table 3-2, the applicability of reactions depending on the types of aldehyde and amine can be seen. As a result of the reactions of N, N-diisopropyl-ethylamine with 4-nitro, 3-nitro and 2-nitro benzaldehydes (Entry 1, Entry 5 and Entry 9), products (1c, 5c and 9c) having two isopropyl groups were synthesized at yields of 75%, 70% and 69%, respectively.

Also, as a result of the reactions of triethylamine with 4-nitro and 4-cyano benzaldehydes (Entry 2 and Entry 14), products (2c and 14c) having two ethyl groups were synthesized at yields of 65% and 67%, respectively.

Further, when 4-nitro benzaldehyde and diisopropylamine (Entry 10) were used, N, N-diisopropyl-4-nitrobenzamide (1c and 10c) was obtained as in a case where N, N-diisopropylethylamine (Entry 1) was used. This means that the present method is operated with a secondary amine. A product N, N-dicyclohexyl-4-nitrobenzamide (6c), which was produced when another secondary amine N, N-dicyclohexylamine (Entry 6) was used, was synthesized at a yield of 62%.

Also, the reactions of tributylamine as a tertiary amine with 4-nitro, 3-nitro, 2-nitro and 4-cyano benzaldehydes (Entry 4, Entry 8, Entry 12 and Entry 16) were conducted. The resultant products 4c, 8c, 12c and 16c were synthesized at yields of 70%, 73%, 15% and 69%, respectively.

Further, the reactions of aldehyde with different tertiary amines (Entry 3, Entry 11 and Entry 15) were conducted. The resultant products 3c, 11c and 15c were synthesized at yields of 57%, 59% and 61%, respectively.

Finally, the reaction of 3-nitro benzaldehyde with aniline (Entry 7) was conducted to check a reaction with a primary amine, and the resultant product 4-nitro-N-phenylbenzamide (7c) was obtained at a yield of 66%. Further, the product 4-nitro-N-butylbenzamide (13c) as a result of reaction of 4-cyano benzaldehyde with butylamine (Entry 13) was obtained at a yield of 73%. Accordingly, it was confirmed that the reaction is operated with a primary amine.

It was concluded from Example 3 that the method of the present disclosure is operated with all of primary, secondary and tertiary amines.

Example 4

(A) of FIG. 3 is a graph showing the changes in yield of a product over reaction time. (B) of FIG. 3 is a graph showing the changes in yield of a product depending on the number of uses of a catalyst.

To check the yield of a product at different times, the yield of a product depending on reaction time was tested. The reactions were conducted for 4 hours, 8 hours, 12 hours, 16 hours and 20 hours, respectively.

Also, to check the efficiency depending on the number of uses of a catalyst, the catalyst was removed by centrifugation after reaction. The test was performed five times with the collected catalyst to check the efficiency of the catalyst.

As shown in (A) of FIG. 3, the yield of the product increased at 4 h and maximized to 75% after 16 hours. Even after the reaction time increased to 20 hours, the yield did not increase. Therefore, it was concluded that the optimum reaction time was 16 hours.

Referring to (B) of FIG. 3, when the catalyst was used for the second time, the yield was the same as that obtained when the catalyst was used for the first time. When the catalyst was used for the third time, the fourth time and the fifth time, the yields were 72%, 68% and 65%, respectively. There was a slight difference but not a significant change in yield. This result shows the recycling capacity of the catalyst.

Example 5

In the presence of the reduced titanium dioxide photocatalyst, nicotine was reacted with each of 4-nitro benzaldehyde and 4-cyano benzaldehyde to make two kinds of biologically active molecules.

The following Reaction Formula 2 is a chemical formula showing a process of synthesizing nicotine-based biologically active molecules having an amide bond by reacting nicotine with aldehyde in the presence of the reduced titanium dioxide according to Example 6 of the present disclosure.

[Reaction Formula 2]

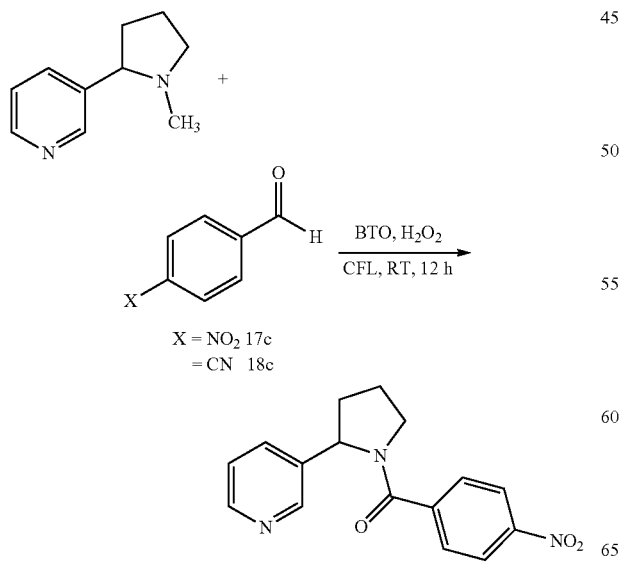

A process of preparing two kinds of biologically active molecules 17c and 18c can be seen from Reaction Formula 2. This shows that the biologically active molecules were synthesized by a cheap and simple method.

Test Example 1

To check whether the reduced titanium dioxide (Blue $TiO_2$) serves as a photocatalyst in the presence of visible light, after irradiation of light from a CFL lamp, EPR spectra of P25 $TiO_2$ and Blue $TiO_2$ were recorded.

FIG. 4 is a graph showing EPR spectra of P25 $TiO_2$ and a reduced titanium dioxide (Blue $TiO_2$) after irradiation of light from a CFL lamp according to Test Example 1 of the present disclosure.

Referring to FIG. 4, when light was irradiated from the CFL lamp, Blue $TiO_2$ exhibited an EPR signal with a high intensity, whereas P25 did not exhibit an EPR signal. This shows that P25 does not generate radicals in the presence of visible light, whereas Blue $TiO_2$ generates radicals in the presence of visible light.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and exemplary embodiments conceived from the meaning and scope of the claims and their equivalents are included in the scope of the present disclosure.

What is claimed is:

1. A preparing method of a compound including an amide group, comprising:
    a process of forming a reduced titanium dioxide which is formed by mixing a titanium dioxide ($TiO_2$) having an anatase phase and a rutile phase with a reducing agent and selectively reducing any one of the anatase phase and the rutile phase; and
    a process of preparing a compound including an amide group by reacting a tertiary amine with a compound represented by Chemical Formula 4:

[Chemical Formula 4]

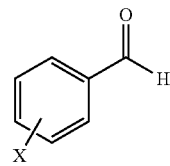

wherein X is $-NO_2$ or CN, and
wherein, the reacting the tertiary amine with the compound represented by Chemical Formula 4 is carried out in the presence of hydrogen peroxide ($H_2O_2$), irradiating light and the reduced titanium dioxide as a photocatalyst.

2. The preparing method of a compound including an amide group according to claim 1, wherein the tertiary amine includes a compound represented by Chemical Formula 1, Chemical Formula 2 or Chemical Formula 3:

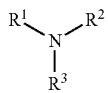
[Chemical Formula 1]

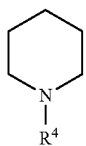
[Chemical Formula 2]

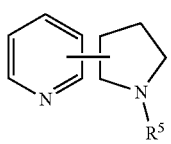
[Chemical Formula 3]

wherein, in Chemical Formulas 1 to 3, $R^1$, $R^2$, $R^3$, $R^4$ and $R^5$ each represent independently linear or branched substituted $C_1$-$C_{20}$ alkyl, or substituted $C_6$-$C_{24}$ aryl; and the substitution is selected from the group consisting of substitution with oxygen, nitrogen, sulfur, linear or branched $C_1$-$C_6$ alkyl, $C_6$-$C_{20}$ aryl, halogen, alkoxy, trimethylsilyl, and ether.

3. A preparing method of a compound including an amide group, comprising:
   a process of forming a reduced titanium dioxide which is formed by mixing a titanium dioxide ($TiO_2$) having an anatase phase and a rutile phase with a reducing agent and selectively reducing any one of the anatase phase and the rutile phase; and
   a process of preparing a compound including an amide group by reacting a tertiary amine with a compound represented by Chemical Formula 5:

$R^6$CHO    [Chemical Formula 5]

wherein $R^6$ is substituted $C_6$-$C_{24}$ aryl and the substitution is selected from the group consisting of $NO_2$ and CN, and wherein, the reacting the tertiary amine with the compound represented by Chemical Formula 5 is carried out in the presence of hydrogen peroxide ($H_2O_2$), irradiating light and the reduced titanium dioxide as a photocatalyst.

4. The preparing method of a compound including an amide group according to claim 1, wherein the process of preparing the compound including the amide group by reacting the tertiary amine in the presence of the reduced titanium dioxide is performed at room temperature.

5. The preparing method of a compound including an amide group according to claim 1, wherein the reducing agent is selected from the group consisting of alkali metals, amines, and a combination thereof.

6. The preparing method of a compound including an amide group according to claim 5, wherein the alkali metals are selected from the group consisting of Li, Na, K and combinations thereof.

7. The preparing method of a compound including an amide group according to claim 5, wherein the amines include a liquid ammonium-based material selected from the group consisting of ethylenediamine, propylenediamine, methylenediamine, ethylamine, 1,2-dimethoxyethane, hexamethyleneimine, diisopropylamide, diethanolamine, polyethyleneamine and combinations thereof, a member selected from the group consisting of ethylenediaminetetraacetic acid, diethylenetriamine pentaacetic acid, diaminohydroxypropane tetraacetic acid and combinations thereof, or a liquid amine for forming solvated electrons, selected from the group consisting of tetrahydrofuran, dimethyl sulfoxide, hexamethylphosphoramide, diethylamine, triethylamine, diethylenetriamine, toluenediamine, m-phenylenediamine, diphenylmethane diamine, hexamethylenediamine, triethylenetetramine, tetraethylenepentamine, hexamethylenetetramine, ethanolamine, diethanolamine, triethanolamine and combinations thereof.

8. The preparing method of a compound including an amide group according to claim 1, wherein the reduction is performed in a sealed and anhydrous state.

9. The preparing method of a compound including an amide group according to claim 1, wherein the reduction is performed at room temperature.

* * * * *